(12) United States Patent
Dempcy et al.

(10) Patent No.: US 6,962,991 B2
(45) Date of Patent: Nov. 8, 2005

(54) PROCESS FOR THE SYNTHESIS OF PYRAZOLOPYRIMIDINES

(75) Inventors: Robert O. Dempcy, Kirkland, WA (US); A. David Adams, Snohomish, WA (US); Michael W. Reed, Seattle, WA (US); Yevgeniy S. Belousov, Mill Creek, WA (US)

(73) Assignee: Epoch Biosciences, Inc., Bothell, WA (US)

( * ) Notice: Subject to any disclaimer, the term of this patent is extended or adjusted under 35 U.S.C. 154(b) by 0 days.

(21) Appl. No.: 09/954,624

(22) Filed: Sep. 12, 2001

(65) Prior Publication Data

US 2003/0078413 A1 Apr. 24, 2003

(51) Int. Cl.$^7$ .................. C07H 19/00; C07H 19/04; C07D 239/00; C07D 473/00
(52) U.S. Cl. .................. 536/26.1; 536/22.1; 536/18.7; 536/27.14; 536/124; 544/253; 544/245
(58) Field of Search .................. 536/26.1, 22.1, 536/18.7, 27.14, 124; 544/253, 245

(56) References Cited

U.S. PATENT DOCUMENTS

| 5,652,099 A | 7/1997 | Conrad |
| 5,844,106 A | 12/1998 | Seela et al. |

FOREIGN PATENT DOCUMENTS

| EP | 286028 A2 | 3/1988 |
| WO | WO 01/64589 A2 | 9/2001 |

OTHER PUBLICATIONS

Seela et al., Nucleic Acid Research, vol. 17, No. 3, (1989).*
Seela et al., Helvetica Chimica acta, vol. 71 (1988).*
Wagner et al., Synthesis of 2'–Deoxyribonucleoside 5'–Phosphoramidites; Helv. Cheim. Acta (2002) vol. 83 pp. 2023–2035.

Seela et al., 168. Synthesis of 2'–Deoxyribofuranosides of 8–Aza–7–deazaguanine and Related Pyrazolo[3,4–d]pyrimidines; Helvetica Chimica Acta (1986) vol. 69 pp. 1602–1613.

Seela et al., Synthesis of 7–Halogenated 8–Aza–2'–deoxyguanosines and Related Pyrazolo [3,4–d] pyrimidine 2'–Deoxyribonucleosides; Synthesis (1998), pp. 207–214.

Seela et al. "*Oligonucleotides Containing Pyrazolo {3,4–d} pyrimidines: The Influence of 7–Substituted 8–Aza–7–deaza–2–deoxyguanosines on the Duplex Structure and Stability*" Helvetica Acta, (1999) vol. 82, pp. 1640–1650.

Seela et al. "Alternating d(G–C) 3 and (C–G) Hexanucleotides containing 7–deaza–2'–deoxyguanosine or 8–Aza–7–deaza–2'–deoxyguanosine in place of dG" Nucleic Acid Research (1989), vol. 17 No. 3, pp. 901–910.

Seela et al. "*8–Aza–7–deaza–2–deoxyguanosine*" *Phosphoramidite Synthesis and Properties of Octanucleotides Helvetica Chimica Acta*, (*1988*) vol. 71, pp. 1191–1198.

* cited by examiner

Primary Examiner—James O. Wilson
Assistant Examiner—Michael C. Henry
(74) Attorney, Agent, or Firm—Townsend and Townsend and Crew LLP

(57) ABSTRACT

The present invention provides a nucleoside comprising a pyrazolopyrimidine base and a process for producing the same. In particular, the processes of the present invention comprises using a halogenated pyrazolopyrimidine base and removing the halogen after the base is coupled to a sugar moiety. The presence of the halogen on the nucleoside base allows facile and economical production of a large quantity of nucleosides.

56 Claims, No Drawings

PROCESS FOR THE SYNTHESIS OF PYRAZOLOPYRIMIDINES

FIELD OF THE INVENTION

The present invention relates to a process for producing pyrazolopyrimidines. In particular, the present invention relates to a process for producing a PPG phosphoramidite.

BACKGROUND OF THE INVENTION

PPG phosphoramidite is often used in synthesis of nucleotides and oligonucleotides containing pyrazolopyrimidine base(s). These nucleotides and oligonucleotides are useful in a variety of applications, including as crosslinkable probes for use in therapeutic and diagnostic applications. See for example PCT publication No. WO 90/14353, which is incorporated herein by reference in its entirety. In addition, oligonucleotides in which one or more purine residues have been replaced by pyrazolopyrimidines display enhanced duplex and triplex-forming ability and display enhanced mismatch discrimination ability. See, for example, Belousov et al., *Nucleic Acids Res.*, 1998, 26, 1324–1328 and U.S. Pat. Nos. 5,594,121 and 6,127,121, all of which are incorporated herein by reference in their entirety. Furthermore, PPG containing oligonucleotides have been shown to reduce self-association observed with guanine-rich oligonucleotides and quenching observed when guanine is adjacent to some fluorophore-containing oligonucleotide conjugates. See WO 00/142505.

Conventional syntheses of PPG phosphoramidite involve coupling an activated sugar moiety with a pyrazolopyrimidine base to produce a nucleoside containing pyrazolopyrimidine base. See, for example, Seela et al., *Helv. Chim. Acta*, 1986, 69, 1602–1613. Further reactions are then carried out to produce PPG phosphoramidite. Unfortunately, conventional processes for producing PPG phosphoramidite require a numerous chromatography separations including that of the nucleoside produced from coupling an activated sugar moiety to a pyrazolopyrimidine base. Typically, chromatography purification of a compound is not suitable for a large scale (e.g., tens or hundreds of grams or more) production because a chromatography process is generally time consuming and labor intensive. Moreover, a large scale chromatography purification process requires a correspondingly large amount of chromatography material, e.g., silica gel and chromatography solvent(s), which increases the production cost of PPG phosphoramidite. Because the pyrazolopyrimidine base containing nucleoside is produced relatively early in the conventional synthesis of PPG phosphoramidite, purification of this nucleoside by chromatography is one of the major hindrances in a cost effective large scale PPG phosphoramidite synthesis.

Therefore, there is a need for a process which is amenable for a large scale production of PPG phosphoramidite.

SUMMARY OF THE INVENTION

One aspect of the present invention provides a PPG phosphoramidite comprising a photolabile hydroxy protecting group, wherein said phosphoramidite nucleoside is of the formula:

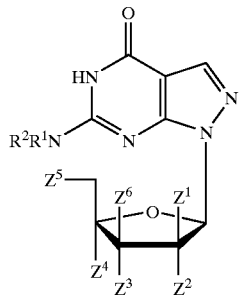

wherein
$R^1$ is selected from the group consisting of hydrogen and alkyl;
$R^2$ is selected from the group consisting of hydrogen, alkyl, and an amine protecting group, or $R^1$ and $R^2$ together form an amine protecting group;
each of $Z^1$, $Z^2$, $Z^4$, and $Z^6$ is independently selected from the group consisting of hydrogen, halide, alkyl, —$OR^{11}$, wherein each $R^{11}$ is independently selected from the group consisting of hydrogen, alkyl, and a hydroxy protecting group or two $R^{11}$ groups form a diol protecting group, or $Z^2$ and $Z^4$ together with the carbon atoms to which they are attached and C-3 carbon atom of the carbohydrate ring form a five-to seven membered ring; and
one of $Z^3$ or $Z^5$ is —$OR^{12}$ and the other is —$OR^{13}$, where $R^{12}$ is a photolabile hydroxy protecting group and $R^{13}$ is a phosphoramidite.

Another aspect of the present invention provides a process for producing a nucleoside or nucleotide comprising a pyrazolopyrimidine base. In particular, the processes of the present invention comprise using a halogenated pyrazolopyrimidine base and removing the halogen after the base is coupled to a sugar moiety. The presence of a halogen on the base allows the nucleoside to be purified by a non-chromatography method, preferably by recrystallization or precipitation. Thus, processes of the present invention allow economical production of a large quantity of nucleosides, including PPG phosphoramidite.

DEFINITIONS

"Alkyl" means a linear or branched saturated monovalent hydrocarbon moiety having from one to ten, preferably one to six, carbon atoms. Exemplary alkyl groups include, but are not limited to, methyl, ethyl, n-propyl, 2-propyl, tert-butyl, pentyl, and the like.

"Nucleoside" refers to a compound comprising a nucleoside base and a sugar which are covalently attached.

"Nucleotide" refers to a compound comprising a nucleoside base, a sugar which are covalently attached to the nucleoside base, and a phosphoryl group which is covalently attached to the sugar.

"Nucleoside base" refers to a non-carbohydrate derivative portion of the nucleoside or nucleotide, including both conventional bases such as purine and pyrimidine bases and their modified versions such as deazapyrimidine, pyrazolopyrimidines and the like.

"Sugar" refers to carbohydrate derivative portion of a nucleoside or nucleotide.

The terms "halo", "halide" and "halogen" are used interchangeably herein and refer to fluoro, chloro, bromo, or iodo, preferably chloro or iodo.

The term "photolabile hydroxy protecting group" refers to hydroxy protecting groups that can be removed under photolytic conditions or a combination of acidic and photolytic conditions.

"Protecting group" refers to a moiety other than an alkyl groups that when attached to a reactive group in a molecule masks, reduces or prevents that reactivity. Examples of protecting groups can be found in Beaucage and Iyer, *Tetrahedron*, 1992, 48, 2223–2311; T. W. Greene and P. G. M. Wuts, *Protective Groups in Organic Synthesis*, 3$^{rd}$ edition, John Wiley & Sons, New York, 1999; and Harrison and Harrison et al., *Compendium of Synthetic Organic Methods*, Vols. 1–8 (John Wiley and Sons, 1971–1996), which are incorporated herein by reference in their entirety. Representative hydroxy protecting groups include acyl groups, benzyl and trityl ethers, tetrahydropyranyl ethers, trialkylsilyl ethers and allyl ethers. Representative amino protecting groups include, formyl, acetyl, trifluoroacetyl, benzyl, benzyloxycarbonyl (CBZ), tert-butoxycarbonyl (Boc), trimethyl silyl (TMS), 2-trimethylsilyl-ethanesulfonyl (SES), trityl and substituted trityl groups, allyloxycarbonyl, 9-fluorenylmethyloxycarbonyl (FMOC), nitro-veratryloxycarbonyl (NVOC), amidines, formamidines, and the like.

The terms "contacting," "treating," and "reacting" when referring to a reaction between two or more reagents are used interchangeably herein and refer to adding two or more reagents into a single reaction vessel, preferably in the presence of a solvent. It should be appreciated, however, the resulting reaction product can be produced directly from a reaction between the added reagents or from an intermediate from one or more of the added reagents which can be produced in the reaction mixture.

"Leaving group" has the meaning conventionally associated with it in synthetic organic chemistry, i.e., an atom or a group capable of being displaced by a nucleophile and includes halo (such as chloro, bromo, and iodo), alkanesulfonyloxy, arenesulfonyloxy, alkylcarbonyloxy (e.g., acetoxy), arylcarbonyloxy, mesyloxy, tosyloxy, trifluoromethanesulfonyloxy, aryloxy (e.g., 2,4-dinitrophenoxy), methoxy, N,O-dimethylhydroxylamino, pixyl and the like.

As used herein, the terms "those defined above" and "those defined herein" when referring to a variable incorporates by reference the broad definition of the variable as well as preferred, more preferred and most preferred definitions, if any.

DETAILED DESCRIPTION

One aspect of the present invention provides a PPG phosphoramidite comprising a photolabile hydroxy protecting group. In particular, the phosphoramidite nucleoside is of the formula:

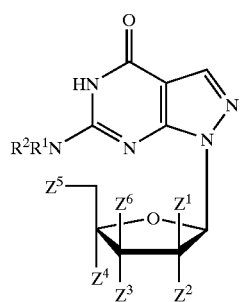

where $R^1$, $R^2$, $Z^1$, $Z^2$, $Z^3$, $Z^4$, $Z^5$ and $Z^6$ are those defined above.

In one particular embodiment of the present invention, the PPG phosphoramidite is of the formula:

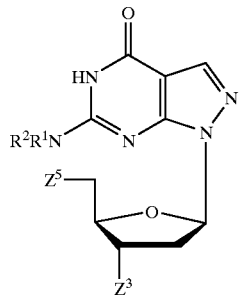

where $R^1$, $R^2$, $Z^3$ and $Z^5$ are those defined above.

In another embodiment of the present invention, $Z^3$ is —$OR^{13}$ and $Z^5$ is —$OR^{12}$, where $R^{12}$ and $R^{13}$ are those defined above.

The photolabile hydroxy protecting group can be any conventional photolabile hydroxy protecting group that is used in nucleotide synthesis. Such photolabile hydroxy protecting groups are well known to one skilled in the art and exemplified, for example, in U.S. Pat. Nos. 5,889,165; 5,744,101; 5,744,305; and 5,489,678 as well as in "*DNA Arrays Methods and Protocols*," Methods in Molecular Biology, by McGall, G. H. and Fidanza, J. A., and edited by Rampal J. B., Vol. 170, pp. 71–101, Humana Press, Inc., 2001, New York, N.Y., and in "*Protection of Nucleosides for Oligonucleotide Synthesis*," Current Protocols in Nucleic Acid Chemistry, ed. by Boyle, A. L., John Wiley & Sons, Inc., 2000, New York, N.Y., all of which are incorporated herein by reference in their entirety. Preferably, the photolabile hydroxy protecting group is selected from the group consisting of α-methyl-6-nitropiperonyloxycarbonyl (i.e, MeNPOC); o-nitrophenylethoxycarbonyl; o-nitrophenylethoxysulfonyl; 3',5'-dimethoxybenzoinoxycarbonyl and derivatives thereof, including but not limited to 2-(2-nitrophenyl)-2-methylethoxycarbonyl and 2-(2-nitro-6-chlorophenyl)-2-methylethylsulfonyl. As used herein the term "derivatives thereof" refers to compounds that have one or more substituents on the aromatic (e.g., phenyl) ring or the alkylene chain portion of the photolabile hydroxy protecting group. For example, the phenyl ring moiety can further comprise one or more substituents such as alkoxy, alkyl, halide, cyano, amino, hydroxy, and nitro; and the alkylene chain portion can be substituted with alkyl, optionally substituted aryl, halide and alkoxy.

Preferably, $R^1$ and $R^2$ together form an amine protecting group. More preferably, $R^1$ and $R^2$ together form an amine protecting group of the formula: =CH—N(CH$_3$)$_2$.

Another aspect of the present invention provides a process for producing a nucleoside. In particular, processes of the present invention utilize a halogenated nucleoside base to produce a non-halogenated nucleoside base containing nucleoside. In particular, the present inventors have found that the presence of a halogen on the nucleoside base allows the resulting nucleoside to be purified by methods other than chromatography, preferably by recrystallization or precipitation, thereby allowing a large scale synthesis of a variety of nucleosides or nucleotides. In addition, purification by recrystallization or precipitation significantly reduces the cost of producing a variety of nucleosides.

The process of the present invention includes contacting a halogenated nucleoside base with an activated sugar under conditions sufficient to produce a halogenated nucleoside base containing nucleoside. The halogenated nucleoside base is then reduced under conditions sufficient to produce a non-halogenated nucleoside base containing nucleoside. Preferably, the halogenated nucleoside base portion of the nucleoside is reduced by hydrogenation in the presence of a hydrogenation catalyst.

The processes of the present invention result in at least about 50% yield of the non-halogenated nucleoside base containing nucleoside from the halogenated nucleoside base. Preferably, the yield is at least about 70%, and more preferably at least about 87%.

The non-halogenated nucleoside base containing nucleoside can be further be converted to a phosphoramidite nucleoside, i.e., a nucleoside comprising a phosphoramidite functional group attached to the sugar portion of the nucleoside. The phosphoramidite nucleosides are useful intermediates in a synthesis of a variety of oligonucleosides and oligonucleotides.

In one aspect, the present invention provides a process for producing a nucleoside comprising a hydropyrazolopyrimidine nucleoside base. The process comprises hydrolyzing and reducing or reducing and hydrolyzing an iodopyrazolopyrimidine nucleoside of the formula:

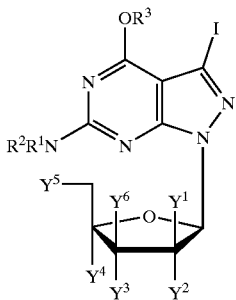

I under conditions sufficient to produce a hydropyrazolopyrimidine nucleoside of the formula:

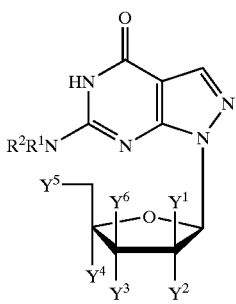

II wherein $R^1$ is selected from the group consisting of hydrogen and alkyl;

$R^2$ is selected from the group consisting of hydrogen, alkyl, and an amine protecting group, or $R^1$ and $R^2$ together form an amine protecting group;

$R^3$ is selected from the group consisting of alkyl, and a hydroxy protecting group; and each of $Y^1$, $Y^2$, $Y^3$, $Y^4$, $Y^5$, and $Y^6$ is independently selected from the group consisting of hydrogen, halide, alkyl, —$OR^4$, wherein each $R^4$ is independently selected from the group consisting of hydrogen, alkyl, and a hydroxy protecting group or two $R^4$ groups form a diol protecting group, e.g., acetonide, or $Y^2$ and $Y^4$ together with the carbon atoms to which they are attached and the carbon atom bearing $Y^3$ and $Y^6$ substituents (i.e., C-3 carbon atom of the carbohydrate ring) form a five-to seven membered ring. Such compounds are sometimes referred to as "locked" nucleic acids, and examples of preparing locked nucleic acids are illustrated by Singh et al., Chem. Comm., 1998, 455–456; and Wengel, Acc. Chem. Res., 1998, 32, 301–310, which are incorporated herein by reference in their entirety.

When $R^4$ is a hydroxy protecting group, preferably it is selected from the group consisting of an acid labile hydroxy protecting group and a photolabile hydroxy protecting group. More preferably $R^4$ is selected from the group consisting of dimethoxytrityl, trityl, pixyl, 1,1-bis(4-methoxyphenyl)-1-pyrenylmethyl (i.e., BMPM), α-methyl-6-nitropiperonyloxycarbonyl, 2-(2-nitrophenyl)-2-methylethoxycarbonyl, 2-(2-nitro-6-chlorophenyl)-2-methylethylsulfonyl and 3',5'-dimethoxybezoinoxycarbonyl.

The hydrolysis reaction replaces the alkoxide group (—$OR^3$) with a hydroxy group (—OH). Preferably, hydrolysis is conducted in an aqueous solution in the presence of a base. Suitable bases include hydroxides, such as sodium hydroxide, lithium hydroxide, potassium hydroxide, calcium hydroxide, magnesium hydroxide; and the like. While a hydroxide is a preferred base, it should be appreciated that any base which has sufficient pKa to generate a hydroxide moiety from water can also be used. Alternatively, the hydrolysis reaction can also be conducted using an acid catalyst, e.g., 2M aqueous HCl at 80° C., see for example, J. Chem. Soc. Chem. Comm., 1990, 19, 1380–1382.

The hydrolysis reaction temperature depends on a variety of factors including concentration of each reagent, reaction medium, reaction time, etc. Typically, however, the hydrolysis reaction temperature is in the range of from about 60° C. to about 105° C. Preferably, the hydrolysis is conducted at a reaction temperature of from about 70° C. to about 100° C., more preferably from about 80° C. to about 95° C., and most preferably from about 85° C. to about 90° C.

The reaction time depends on a variety of factors including the concentration of each reagent, reaction temperature, and the base used. Typically, the hydrolysis reaction time in an aqueous solvent in the presence of a hydroxide ranges from about 2 hrs to about 24 hrs, preferably from about 4 hrs to about 12 hrs, and more preferably from about 5 hrs to about 7 hrs. Generally, one skilled in the art will readily recognize that the progress of reaction can be monitored by conventional analytical methods, such as TLC, HPLC and GC.

Hydrogenolysis, e.g., replacement of iodide with hydrogen, can be achieved by any conventional halogen reduction method known to one of ordinary skill in the art. Typically, the iodide is reduced by hydrogenation in the presence of a hydrogenation catalyst. Exemplary hydrogenation catalysts that are useful in reducing iodide to hydrogen include, but are not limited to, palladium, platinum, rhodium, Raney Nickel®, and the like. In one particular embodiment of the present invention, palladium on carbon is used as the hydrogenation catalyst. Preferably, the hydrogenation reaction is conducted near the atmospheric pressure of hydrogen.

Suitable solvents for hydrogenation reaction include, but are not limited to, alcohol, such as methanol, ethanol, isopropanol, and the like; water; DMF; THF; methoxyethanol; and mixtures thereof. Typically water or a solvent mixture comprising water is used as the hydrogenation solvent because the hydrogenation reaction product is soluble in water. Water is also preferred since it is non-flammable and is not subject to the hazards in the presence of active hydrogenolysis catalysts.

The hydrolysis and reduction can be conducted in any sequence. While the product of the first step can be purified prior to conducting a subsequent reaction, it has been found by the present inventors that such purification is not necessary. Typically, the iodopyrazolopyrimidine nucleoside of Formula I is hydrolyzed and the resulting product is subjected to a hydrogenation reaction without any purification. The resulting hydropyrazolopyrimidine nucleoside of Formula II can be conveniently purified by crystallization. Preferably, the yield of hydropyrazolopyrimidine nucleoside of Formula II from the iodopyrazolopyrimidine nucleoside of Formula I using the process of the present invention is at least about 50%, more preferably at least about 70%, and most preferably at least about 90%.

The hydropyrazolopyrimidine nucleoside of Formula II can be used as an intermediate in synthesis of a variety of nucleosides including PPG phosphoramidite.

Thus, in another aspect of the present invention provide a process for producing a PPG phosphoramidite of the formula:

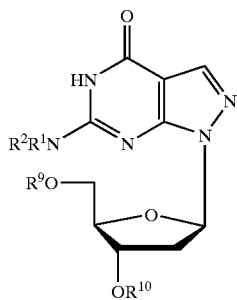

III from the hydropyrazolopyrimidine nucleoside of the formula:

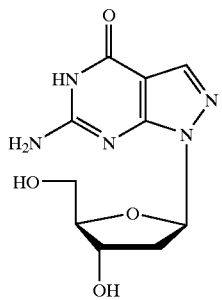

IV wherein $R^1$ is hydrogen and $R^2$ is an amine protecting group or $R^1$ and $R^2$ together form an amine protecting group; and one of $R^9$ and $R^{10}$ is a phosphoramidite and the other is a hydroxy protecting group.

The PPG phosphoramidite producing step comprises:

(a) (i) contacting the hydropyrazolopyrimidine nucleoside of Formula II with an amine protecting reagent under conditions sufficient to produce an amine-protected nucleoside of the formula:

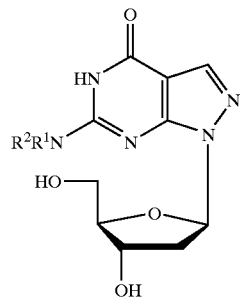

V (ii) contacting the amine-protected nucleoside of Formula V with a hydroxy protecting reagent under conditions sufficient to produce an amine/monohydroxy protected nucleoside of the formula:

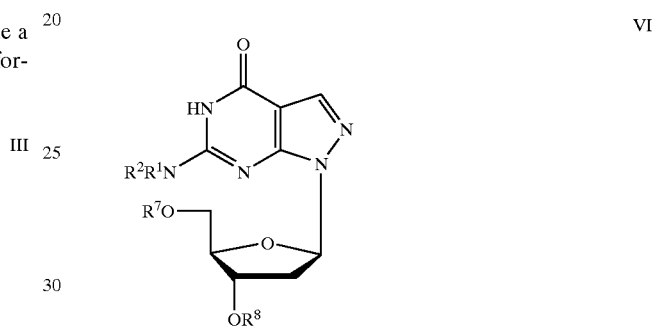

VI or (i) contacting the hydropyrazolopyrimidine of Formula IV with a hydroxy protecting reagent under conditions sufficient to produce a monohydroxy protected nucleoside of the formula:

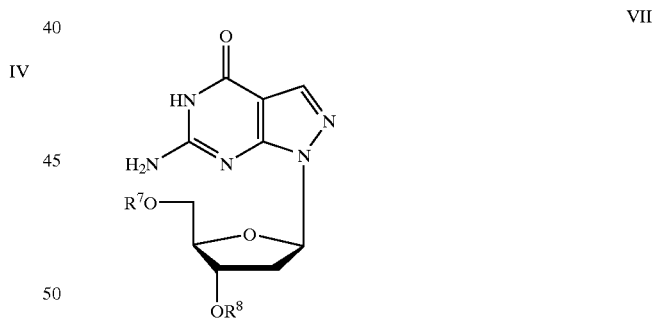

VII (ii) contacting the monohydroxy protected nucleoside of Formula VII with an amine protecting reagent under conditions sufficient to produce the amine/monohydroxy protected nucleoside of Formula VI, wherein $R^1$ is hydrogen and $R^2$ is an amine protecting group or $R^1$ and $R^2$ together form an amine protecting group; and one of $R^7$ and $R^8$ is hydrogen and the other is a hydroxy protecting group; and (b) contacting the amine/monohydroxy protected nucleoside of Formula VI with an activated phosphoramidite under conditions sufficient to produce the PPG phosphoramidite of Formula III.

Any of the conventional amine protecting reagents can be used, such as those disclosed in the above incorporated Beaucage and Iyer, *Tetrahedron*, 1992, 48, 2223–2311; T. W. Greene and P. G. M. Wuts, *Protective Groups in Organic Synthesis*, 3rd edition, John Wiley & Sons, New York, 1999; and Harrison and Harrison et al., *Compendium of Synthetic Organic Methods*, Vols. 1–8 (John Wiley and Sons, 1971–1996). In one particular embodiment, the amine protecting reagent is selected from the group consisting of N,N-dialkyl formamide dialkylacetal, such as N,N-dimethylformamide dimethylacetal; and N,N-dialkylacetamide dialkylacetal, such as N,N-dimethylacetamide dimethylacetal. Reaction conditions for protecting an amino group are well known to one skilled in the art.

Similarly, any of the conventional hydroxy protecting groups can be used in the processes of the present invention, such as those disclosed in the above described *Protective Groups in Organic Synthesis*, 3rd edition. In one particular embodiment, the hydroxy protecting reagent is an acid labile hydroxy protecting reagent, i.e., hydroxy protecting group which can be deprotected (i.e., removed) using an acid. Preferably, the acid labile hydroxy protecting reagent is selected from the group consisting of pixyl halide, such as pixylchloride; trityl halide; monomethoxytrityl halide; dimethoxytrityl halide; and 1,1-bis(4-methoxyphenyl)-1-pyrenylmethyl halide (i.e., BMPM halide). Reaction conditions for protecting a hydroxy group are also well known to one skilled in the art and are also disclosed in the above incorporated Beaucage and Iyer, *Tetrahedron*, 1992, 48, 2223–2311; T. W. Greene and P. G. M. Wuts, *Protective Groups in Organic Synthesis*, 3rd edition, John Wiley & Sons, New York, 1999; Boyle, Ann L. (Editor), *Current Protocols in Nucleic Acid Chemistry*, John Wiley and Sons, New York, 2000; and Harrison and Harrison et al., *Compendium of Synthetic Organic Methods*, Vols. 1–8 (John Wiley and Sons, 1971–1996).

In another embodiment, the hydroxy protecting reagent is a photolabile hydroxy protecting reagent. Suitable photolabile hydroxy protecting reagents are well known to one skilled in the art and include those disclosed in the above incorporated U.S. Pat. Nos. 5,889,165; 5,744,101; 5,744,305; and 5,489,678; and "*DNA Arrays Methods and Protocols*," Methods in Molecular Biology, by McGall, G. H. and Fidanza, J. A., and edited by Rampal J. B., Vol. 170, pp. 71–101, Humana Press, Inc., 2001, New York, N.Y.; and "*Protection of Nucleosides for Oligonucleotide Synthesis*," Current Protocols in Nucleic Acid Chemistry, ed. by Boyle, A. L., John Wiley & Sons, Inc., 2000, New York, N.Y. Preferably, the photolabile hydroxy protecting reagent is selected from the group consisting of 1-(3,4-methylenedioxy-6-nitrophenyl)ethyl chloroformate, 2-(2-nitrophenyl)-2-methylethyl chloroformate, 2-(2-nitro-6-chlorophenyl)-2-methylethylsulfonyl chloride, and 3',5'-dimethoxybezoinoxyl chloroformate.

Nucleosides of the present invention comprising a hydropyrazolopyrimidine nucleoside base and a photolabile hydroxy protecting group on the sugar moiety are useful in a variety of applications. In particular, these nucleosides are useful in synthesizing a library of oligonucleotides (i.e., array of oligonucleotides) using conventionally well known solid phase oligonucleotide array synthesis such as those disclosed in the above incorporated U.S. Pat. Nos. 5,889,165; 5,744,101; 5,744,305; and 5,489,678; and "*DNA Arrays Methods and Protocols*," Methods in Molecular Biology, by McGall, G. H. and Fidanza, J. A., and edited by Rampal J. B., Vol. 170, pp. 71–101, Humana Press, Inc., 2001, New York, N.Y.

In one aspect of the present invention, the activated phosphoramidite is of the formula:

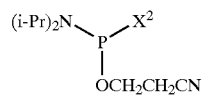

VIII where $X^2$ is a leaving group, preferably halide or diisopropylamino, i.e., a moiety of the formula —N(i-Pr)$_2$. The reaction between the activated phosphoramidite of Formula VIII and the amine/monohydroxy protected nucleoside of Formula VI is typically carried out at a temperature range of from about 0° C. to about 40° C., preferably from about 10° C. to about 35° C., and more preferably from about 20° C. to about 30° C. Suitable reaction solvents are inert organic solvents, including halogenated organic solvents, such as methylene chloride and chloroform; ethers, such as tetrahydrofuran and diethyl ether; aromatic hydrocarbons, such as toluene, xylenes and halogenated phenyls; hydrocarbons; and other organic solvents which are substantially inert to the reaction conditions and in which the reagents are soluble. It should be appreciated that when organic solvents which have a higher boiling point is used, the reaction temperature range can correspondingly be extended.

The processes of the present invention can also include producing the nucleoside of Formula I, which comprises contacting an iodopyrazolopyrimidine of the formula:

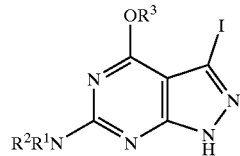

IX with an activated sugar of the formula:

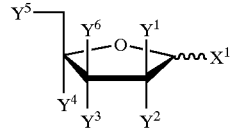

X under conditions sufficient to produce the nucleoside of Formula I, where $R^1$, $R^2$, $R^3$, $Y^1$, $Y^2$, $Y^3$, $Y^4$, $Y^5$, and $Y^6$ are those defined above; and $X^1$ is a leaving group. Preferably, $X^1$ is a halide, and more preferably chloride.

Generally, the process for producing the nucleoside of Formula I involves contacting the iodopyrazolopyrimidine of Formula IX with a base having a sufficient pKa to deprotonate the pyrazolyl nitrogen atom and contacting the deprotonated iodopyrazolopyrimidine with the activated sugar of Formula X. Such deprotonation of the iodopyrazolopyrimidine of Formula IX by the base can occur in situ, as described in detail below. The reaction temperature for producing the nucleoside of Formula I is typically in the range of from about 5° C. to about 60° C., preferably from about 10° C. to about 40° C., and more preferably from about 20° C. to about 30° C. Suitable reaction solvents include, but are not limited to, alcohols, such as methanol, ethanol, isopropanol, and the like; relatively polar organic solvents, such as DMF and acetonitrile; water; and mixtures thereof.

Alternatively, the iodopyrazolopyrimidine of Formula IX and the activated sugar of Formula X can be combined in a reaction vessel in the presence of a base. In this alternative embodiment, the reaction conditions are selected such that the reaction rate between the iodopyrazolopyrimidine of Formula IX and the activated sugar of Formula X is significantly higher than the reaction rate between the base and the activated sugar of Formula X.

Useful bases for producing the nucleoside of Formula I from the iodopyrazolopyrimidine of Formula IX and the activated sugar of Formula X include, but are not limited to, bases in which the corresponding acids have pKa of at least about 9, preferably at least about 10, and more preferably at least about 12. Exemplary bases include, but are not limited to, alkoxides, such as alkaline or alkaline-earth metal methoxides, ethoxides, propoxides, isopropoxides, butoxides, tert-butoxides, and the like; hydrides, such a as sodium hydride, calcium hydride, potassium hydride, and the like; and organic bases, such as amines, e.g., tertiary amines, DBU and DBN.

The processes of the present invention provide the nucleoside of Formula I from the iodopyrazolopyrimidine of Formula IX and the activated sugar of Formula X at a yield of at least about 35%. Preferably, the yield is at least about 50%, and more preferably at least about 65%.

The processes of the present invention can also include producing the iodopyrazolopyrimidine of Formula IX (e.g., where $R^1$ and $R^2$ are hydrogen) comprising:

(i) contacting a pyrimidinone of the formula:

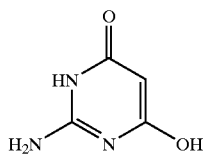

XI with a halogenating agent and a formylating agent under conditions sufficient to produce a dihalopyrimidine carboxyaldehyde of the formula:

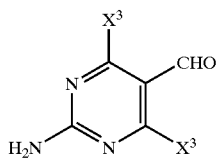

XII where each $X^3$ is independently selected from the group consisting of F, Cl, Br and I;

(ii) contacting the dihalopyrimidine carboxyaldehyde of Formula XII with hydrazine under conditions sufficient to produce a halopyrazolopyrimidine of the formula:

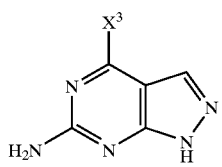

XIII (iii) contacting the halopyrazolopyrimidine of Formula XIII with an alkoxide of the formula $R^3$—OM, where $R^3$ is alkyl and M is a metal, to produce an alkoxypyrazolopyrimidine of the formula:

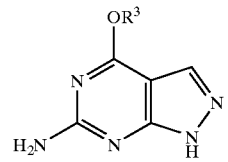

XIV and (iv) iodinating the alkoxypyrazolopyrimidine of Formula XIV with an iodinating agent under conditions sufficient to produce the iodopyrazolopyrimidine of Formula IX.

Preferably, the halogenating agent is selected from the group consisting of $POCl_3$, iodine monochloride (i.e., ICl), N-iodosuccinamide and $SOCl_2$. The formylation and halogenation reactions can be conveniently conducted in a single reaction condition. For example, when $POCl_3$ is used as the halogenating agent, dimethyl formamide (DMF) can be used as a reaction solvent and a formylating agent to provide the dihalopyrimidine carboxyaldehyde of Formula XII directly from the pyrimidinone of Formula XI. In this embodiment, the reaction mixture is typically combined at about 0° C. The resulting mixture then is heated to a temperature range of from about 40° C. to about 100° C., preferably from about 60° C. to about 100° C., and more preferably from about 90° C. to about 98° C. The resulting dihalopyrimidine carboxyaldehyde of Formula XII precipitates out of an aqueous solution and can be further purified by recrystallization. The yield of combined formylation and halogenation reaction is typically at least about 50%, preferably at least about 60%, and more preferably at least about 70%. Other suitable Vilsmeier formylation/halogenating reagent combinations include any compound having a formyl group attached to a secondary amino group in combination with a halogenating agent. Exemplary formylating reagents include 1-formylpiperidine, 1-formylmorpholine and triformamide. Exemplary halogenating agents include oxalyl chloride, $PCl_5$, $Br_2/PPh_3$ and $SOX_2$, where X is Cl or Br.

Reacting the dihalopyrimidine carboxyaldehyde of Formula XII with hydrazine then affords the halopyrazolopyrimidine of Formula XIII. Alternatively, hydrazine monohydrate can be used rather than anhydrous hydrazine. Typically, this reaction is conducted in the presence of a base, preferably a trialkyl amine base, such as triethylamine. The resulting halopyrazolopyrimidine of Formula XIII can be purified by recrystallization.

The halopyrazolopyrimidine of Formula XIII is then reacted with an alkoxide of the formula $R^3$—OM, where $R^3$ is alkyl and M is a metal, to displace the halide ($X^3$), thereby producing the alkoxypyrazolopyrimidine of Formula XIV. It should be appreciated that while the empirical formula of the alkoxide is written as $R^3$-OM, depending on the nature of the metal, there can be more than one alkoxide group per metal. For example, when the metal is a divalent metal, e.g., alkaline earth metal or a transition metal such as Mg or Ca, the valence of these metals are +2; therefore, there are two alkoxide groups associated with each metal in the empirical formula. Displacement of the halide ($X^3$) by the alkoxide is conveniently carried out in an alcoholic solvent, preferably the alcohol corresponding to the alkoxide. Generally, the reaction is heated, preferably to the solvent's refluxing temperature, to facilitate the reaction. The resulting mixture is then cooled, neutralized by adding an acid, and precipitated to afford the alkoxypyrazolopyrimidine of Formula XIV.

Reaction of the alkoxypyrazolopyrimidine of Formula XIV with a halogenating agent provides a halogenated nucleoside base. The present inventors have found that the presence of a halogen on the nucleoside base allows purification of the resulting halogenated nucleoside base containing nucleoside by recrystallization; thus, providing a means for a cost effective large scale nucleoside synthesis. The halogen can be chlorine, bromine or iodine; however, iodine is preferred as it provides the highest mass. Without being bound by any theory, it is generally believed that high mass is one of the factors that contribute in the compound being a solid, which allows the compound to be purified by recrystallization or precipitation.

Iodination of the alkoxypyrazolopyrimidine of Formula XIV can be affected by any electrophilic iodinating agent which is compatible with functional groups that are present in the alkoxypyrazolopyrimidine of Formula XIV. Exemplary iodinating agents include iodine monochloride, N-iodosuccinimide and other iodinating agents known to one skilled in the art. Preferably, the iodinating agent is selected from the group consisting of iodine monochloride and N-iodosuccinimide.

In one particular embodiment, the iodopyrazolopyrimidine of Formula IX is produced by reacting the alkoxypyrazolopyrimidine of Formula XIV with iodine monochloride. Typically, the iodination is conducted in an aqueous solution under refluxing conditions. The reaction can also include adding a mild base to neutralize or buffer the effect of acid that is generated in the reaction mixture. Suitable mild bases include carboxylates, such as metal acetates; and other salts of acids having a pKa of from about 4 to about 6. After the reaction, any remaining iodide monochloride is destroyed (i.e., neutralized, removed or converted to other compound) by adding a reducing agent such as sodium metabisulfite or other suitable reducing agents. Preferably, the reaction solvent is selected such that the resulting iodopyrazolopyrimidine of Formula IX precipitates out of the reaction mixture, which can be further purified by dissolving in hot DMF and precipitating it by addition of water.

Additional objects, advantages, and novel features of this invention will become apparent to those skilled in the art upon examination of the following examples thereof, which are not intended to be limiting.

EXAMPLES

Example 1

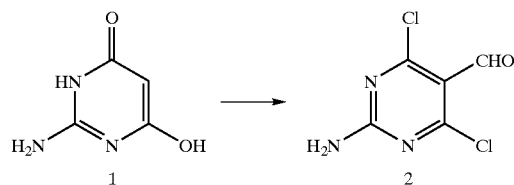

This example illustrate a method for producing 2-amino-4,6-dichloropyrimidine-5-carboxaldehyde (2).

Absolute DMF (210 ml, 1.38 mol) was added drop wise to an ice-cold solution of POCl$_3$ (900 ml) over a 20 min period. The ice-bath was removed and 150 g (1.17 mol) of powdered 2-amino-6-hydroxypyrimidine-4(3H)-one (1) was added over a 20 min period. The mixture was then heated to 100° C. and stirred for 3–4 h. The solution was cooled to room temperature and poured into 10 L of ice water (4L of crushed ice diluted to 10L with water). This aqueous solution was then heated to 50° C. and stirred for 2 h. The mixture was refrigerated overnight and the precipitate was filtered and dried to provide 160 g (71% yield) of 2-amino-4,6-dichloropyrimidine-5-carboxaldehyde (2).

Example 2

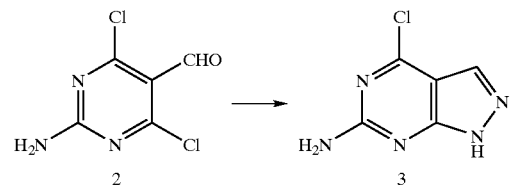

This example illustrate a method for producing 4-chloro-6-aminopyrazolo[3,4-d]pyrimidine (3).

To a mixture of 2-amino-4,6-dichloropyrimidine-5-carboxaldehyde (2) (150 g, 0.785 mol), THF (2.7 L) and triethylamine (125 ml) was added anhydrous hydrazine (25.5 ml in 600 ml of water) drop wise over 25 min. Alternatively, hydrazine monohydrate can be used instead of anhydrous hydrazine. The mixture was stirred for 1 h. The solids were filtered off and the filtrate was evaporated to remove about 80% of the THF. Water was added and the resulting precipitate was filtered and dried under vacuum. The solid was then dissolved in a minimum volume of hot DMF and precipitate by addition of water to provide 112 g (85% yield) of 4-chloro-6-aminopyrazolo[3,4-d]pyrimidine (3).

Example 3

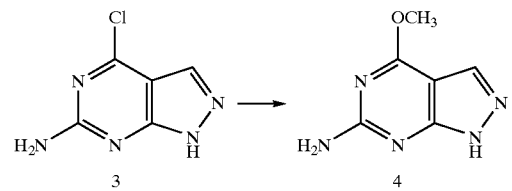

This example illustrates a method for producing 4-methoxy-6-aminopyrazolo[3,4-d]pyrimidine (4).

Compound 3 (70.4 g, 0.416 mol) was refluxed in methanolic sodium methoxide solution (25 g sodium dissolved in 1 L methanol) for 2 h. The reaction mixture was cooled to room temperature and neutralized by addition of acetic acid (75 ml). The mixture was evaporated to dryness and the solid was triturated in 600 ml of water, filtered and dried to provide 67.5 g (99% yield) of 4-methoxy-6-aminopyrazolo[3,4-d]pyrimidine (4).

Example 4

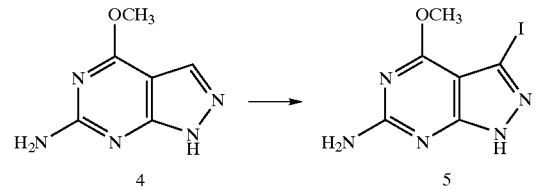

This example illustrates a method for producing 3-iodo-4-methoxy-6-aminopyrazolo[3,4-d]pyrimidine (5).

A mixture of compound 4 (105 g, 0.636 mol), sodium acetate (263 g) and iodine monochloride (140 g) was mechanically stirred in 1.3 L of water at a temperature between 92–98° C. for 5 h. The mixture was cooled to room temperature and a solution of sodium metabisulfite (139 g in 500 ml of water) was added. The mixture was stirred for 10 minutes and then filtered. The solid was rinsed with water and dried. The resulting dried solid was dissolved in 840 ml of hot DMF and precipitate by addition of 800 ml of water. The mixture was cooled in an ice-bath and the solid was filtered and dried to provide 144 g (78% yield) of 3-iodo-4-methoxy-6-aminopyrazolo[3,4-d]pyrimidine (5).

Example 5

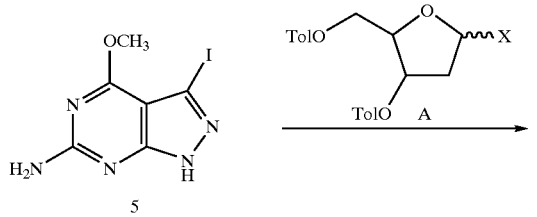

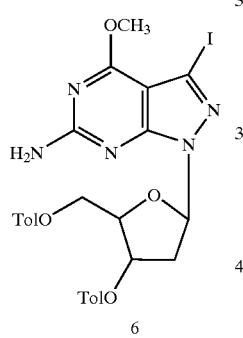

This example illustrates a method for producing 3-iodo-4-methoxy-6-amino-1-(2-deoxy-3,5-di-O-toluoyl-β-D-erythro-pentofuranosyl) 1H-pyrazolo[3,4-d]pyrimidine (6).

To a suspension of Compound 5 (67 g, 0.230 mol) in 650 ml of methanol was added a solution of 15.22 g KOH (15% water by weight) dissolved in 100 ml of methanol. The mixture was stirred for 5 min and then evaporated to dryness. The solid was dissolved in 270 ml of anhydrous DMF and then diluted with 1.55 L of anhydrous acetonitrile (i.e., MeCN). The chlorosugar derivative A (107 g) was added immediately after the MeCN dilution. The mixture was stirred vigorously for 2.5 hours and the crude product was filtered. The damp solid was triturated in 350 ml of water, filtered and dried to provide 97.7 g (66% yield) of 3-iodo-4-methoxy-6-amino-1-(2-deoxy-3,5-di-O-toluoyl-β-D-erythro-pentofuranosyl) 1H-pyrazolo[3,4-d]pyrimidine (6).

Example 6

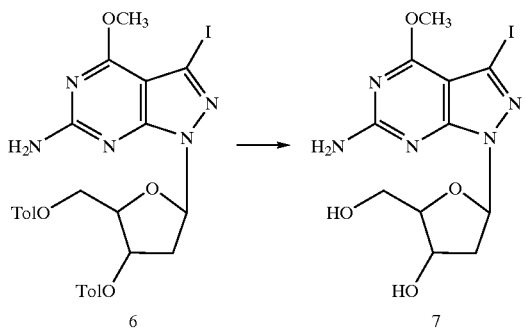

This example illustrates a method for producing 3-iodo-4-methoxy-6-amino-1-(2'-deoxy-β-D-erythro-pentofuranosyl)pyrazolo[5,4-d]pyrimidine (7).

Compound 6 (219 g, 0.341 mol) was suspended in 970 ml of methanol. A solution of 1 M NaOMe in methanol (130 ml) was added and the mixture was refluxed for 1 h. The flask was placed in the freezer for 5 hours and the crystals were filtered and rinsed sparingly with cold methanol to provide 89.6 g (65% yield) of 3-iodo-4-methoxy-6-amino-1-(2'-deoxy-β-D-erythro-pentofuranosyl)pyrazolo[5,4-d]pyrimidine (7).

The yield can be increased to 71% by cooling the reaction mixture in the freezer overnight.

Example 7

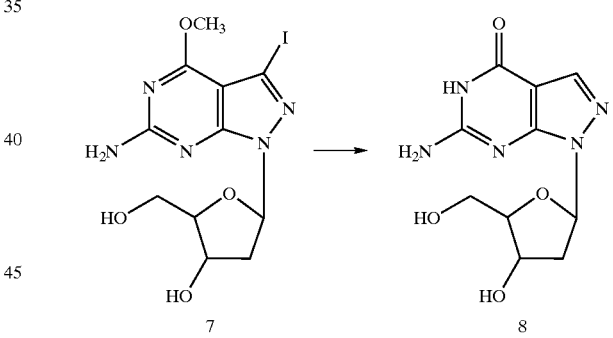

This example illustrates a method for producing 1-(2'-deoxy-β-D-erythro-pentofuranosyl)-6-amino-5-hydropyrazolo[5,4-d]pyrimidine-4-one (8).

Compound 7 (73.35 g, 0.180 mol) was stirred in a solution of 21 g NaOH in 885 ml water at 90° C. for 6 h. The clear solution was cooled to room temperature and then transferred to a hydrogenation bottle containing 3.6 g of 5% Pd/C (50% water content by weight, Aldrich Chemical Co., Milwaukee, Wis.). The mixture was shaken under 40 psi of hydrogen for 90 min. The mixture was filtered through Celite and the filtrate was neutralized to pH 7 using concentrated HCl, followed by a fine pH adjustment with acetic acid. The solution was placed in a refrigerator overnight and the crystals that formed were filtered, rinsed sparingly with ice-cold water, and dried to provide 41.5 g (87% yield) of 1-(2'-deoxy-β-D-erythro-pentofuranosyl)-6-amino-5-hydropyrazolo[5,4-d]pyrimidine-4-one (8).

Example 8

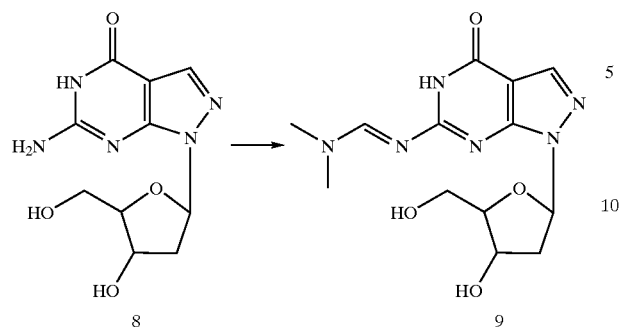

This example illustrates a method for producing 1-(2'-deoxy-β-D-erythro-pentofuranosyl)-6-formadino-5-hydropyrazolo[5,4-d]pyrimidine-4-one (9).

Compound 8 (101 g, 0.378 mol) was dissolved in 325 ml of dry DMF. N,N-Dimethylformamide dimethylacetal (150 ml) was added. The mixture was stirred for 4 hours. The solvents were evaporated off and the residue was twice evaporated from xylenes. The foam was then triturated in 200 ml of absolute ethanol. The mixture was diluted by addition of 1.6 L of ether and the solid was filtered and dried to provide 119 g (97% yield) of 1-(2'-deoxy-β-D-erythro-pentofuranosyl)-6-formadino-5-hydropyrazolo [5,4-d] pyrimidine-4-one (9).

Example 9

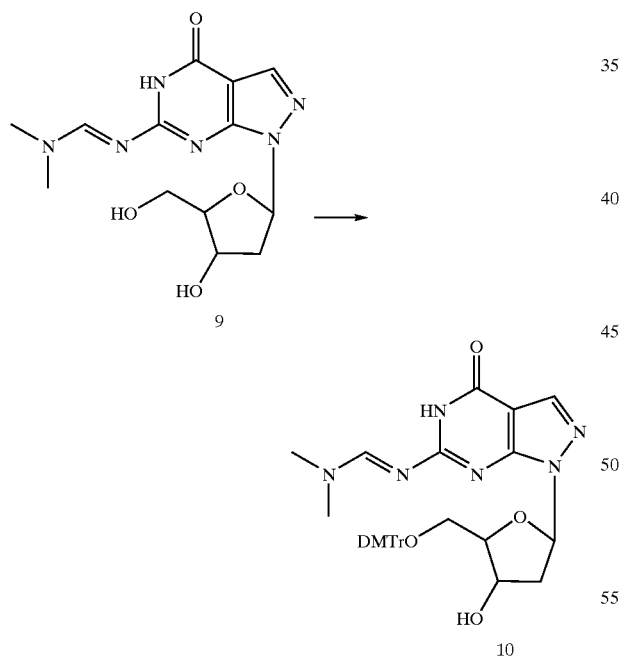

This example illustrates a method for producing an acid labile DMTr hydroxy protecting group derivative of Compound 9.

Dimethoxytrityl chloride (8.0 g) was added to a solution of Compound 9 (6.42 g, 19.92 mmol) in 120 ml dry pyridine. The reaction solution was stirred for 3 h at room temperature. The reaction was monitored by TLC (5% methanol in ethyl acetate) and add more DMTrCl as necessary. The completed reaction solution was poured into 600 ml of 5% sodium bicarbonate. The mixture was extracted with 600 ml of ethyl acetate and the extract was dried over sodium sulfate and evaporated. The residue was purified using silica gel chromatography eluting with 5% methanol in ethyl acetate. The product fractions were evaporated affording 10.6 g (85% yield) of Compound 10 as a foam.

Example 10

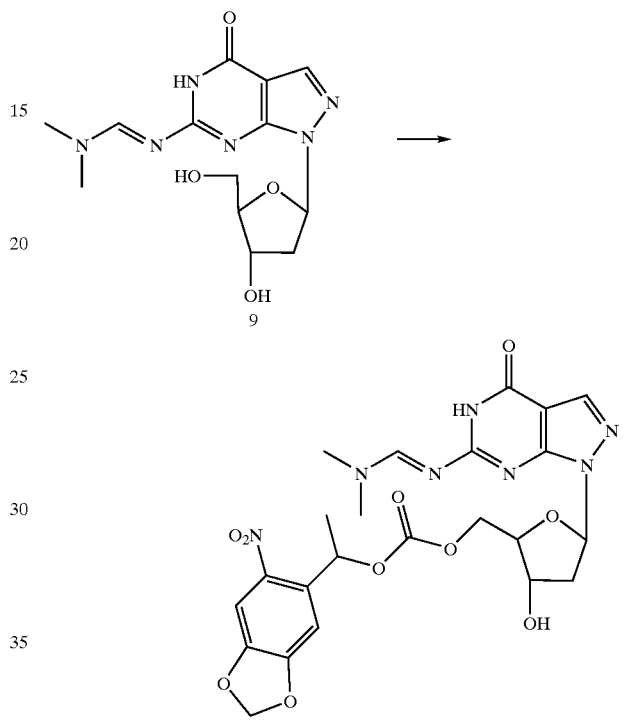

This example illustrates a method for producing a photolabile MeNPOC hydroxy protecting group derivative of Compound 9.

Compound 11 is synthesized by a modified procedure described by McGall, G. H. and Fidanza, J. A., "*DNA Arrays Methods and Protocols,*" Edited by Rampal J. B., Methods in Molecular Biology, 170: 71–101 (2001), Humana Press, Inc., New York, N.Y., in particular sections 3.1.2 and 3.1.3.

Example 11

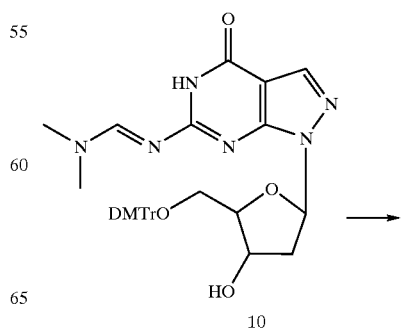

-continued

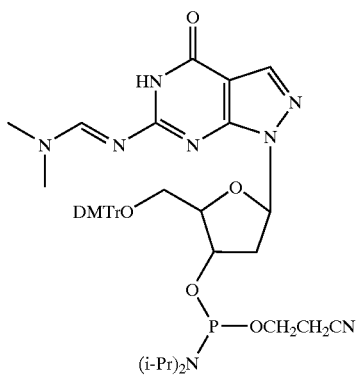

12

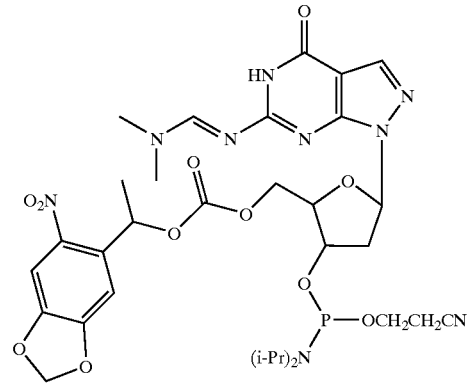

13

This example illustrates a method for producing PPG phosphoramidite (12) comprising an acid labile hydroxy protecting group DMTr.

To a solution of Compound 10 (9.15 g, 14.65 mmol) dissolved in 356 ml of dry methylene chloride, containing 7.6 ml of N,N-diisopropylethylamine, was added 5.5 ml of 2-cyanoethyl diisopropylchlorophosphoramidite. The solution was stirred under argon for 2 hrs. at room temperature. The solution was treated with 10 ml of methanol and then poured into 400 ml of 5% sodium bicarbonate solution. The mixture was extracted with ethyl acetate (500 ml) and the extract was dried over sodium sulfate, filtered and evaporated. The residue was purified by silica gel chromatography eluting with 3% methanol in ethyl acetate (2% triethylamine). The pure product fractions were evaporated. The residue was dissolved in a minimum volume of ether, which was added drop wise to filtered hexanes. The precipitate was filtered and dried to provide 9.8 g (81% yield) of PPG phosphoramidite (12).

Example 12

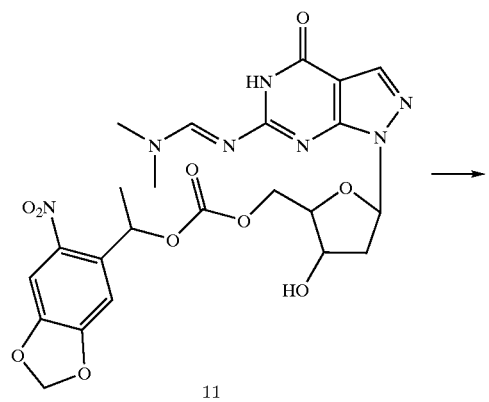

11

→

This example illustrates a method for producing PPG phosphoramidite (13) comprising a photolabile hydroxy protecting group MeNPOC.

Compound 13 is synthesized by a modified procedure described by McGall, G. H. and Fidanza, J. A., "*DNA Arrays Methods and Protocols*," Edited by Rampal J. B., Methods in Molecular Biology, 170: 71–101 (2001), Humana Press, Inc., New York, N.Y., in particular section 3.1.6.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A PPG phosphoramidite comprising a photolabile hydroxy protecting group, wherein said phosphoramidite nucleoside is of the formula:

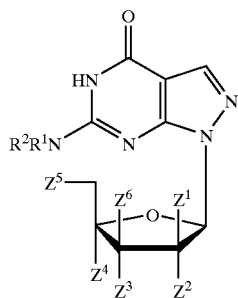

wherein $R^1$ is selected from the group consisting of hydrogen and alkyl;

$R^2$ is selected from the group consisting of hydrogen, alkyl, and an amine protecting group, or $R^1$ and $R^2$ together form an amine protecting group;

each of $Z^1$, $Z^2$, $Z^4$, and $Z^6$ is independently selected from the group consisting of hydrogen, halide, alkyl, —$OR^{11}$, wherein each $R^{11}$ is independently selected from the group consisting of hydrogen, alkyl, and a hydroxy protecting group or two $R^{11}$ groups form a diol protecting group, or $Z^2$ and $Z^4$ together with the carbon atoms to which they are attached and C-3 carbon atom of the carbohydrate ring form a five-to seven membered ring; and one of $Z^3$ or $Z^5$ is —$OR^{12}$ and the other is —$OR^{13}$, where $R^{12}$ is a photolabile hydroxy protecting group and $R^{13}$ is a phosphoramidite.

2. The PPG phosphoramidite according to claim 1 of the formula:

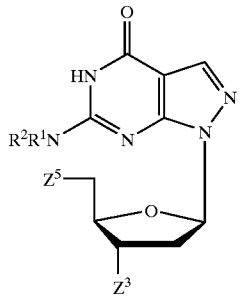

wherein $R^1$, $R^2$, $Z^3$ and $Z^5$ are those defined in claim 1.

3. The PPG phosphoramidite according to claim 2, wherein $Z^3$ is —$OR^{13}$ and $Z^5$ is —$OR^{12}$, where $R^{12}$ is a photolabile hydroxy protecting group and $R^{13}$ is a phosphoramidite.

4. The PPG phosphoramidite according to claim 3, wherein the photolabile hydroxy protecting group is selected from the group consisting of α-methyl-6-nitropiperonyloxycarbonyl, 2-(2-nitrophenyl)-2-methylethoxycarbonyl, 2-(2-nitro-6-chlorophenyl)-2-methylethylsulfonyl, and 3',5'-dimethoxybezoinoxycarbonyl.

5. The PPG phosphoramidite according to claim 4, wherein $R^1$ and $R^2$ together form an amine protecting group.

6. The PPG phosphoramidite according to claim 5, wherein $R^1$ and $R^2$ together form an amine protecting group of the formula: =CH—N(CH$_3$)$_2$.

7. A process for producing a non-halogenated nucleoside base containing nucleoside comprising:
  (a) contacting a halogenated nucleoside base with an activated sugar under conditions sufficient to produce a halogenated nucleoside base containing nucleoside; and
  (b) reducing said halogenated nucleoside base containing nucleoside under conditions sufficient to produce said non-halogenated nucleoside base containing nucleoside.

8. The process of claim 7, wherein said non-halogenated nucleoside base containing nucleoside is purified by recrystallization.

9. The process of claim 7, wherein the yield of said non-halogenated nucleoside base containing nucleoside from said halogenated nucleoside base is at least about 50%.

10. The process of claim 7, wherein said halogenated nucleoside base containing nucleoside reducing step comprises hydrogenation of said halogenated nucleoside base containing nucleoside in the presence of a hydrogenation catalyst.

11. The process of claim 7, further comprising protecting amine and hydroxy groups of the non-halogenated nucleoside base and reacting the resulting product with an activated phosphoramidite to produce a -phosphoramidite nucleoside.

12. The process of claim 11, further comprising incorporating said phosphoramidite nucleoside in an oligonucleoside or an oligonucleotide.

13. A process for producing a nucleoside comprising a hydropyrazolopyrimidine nucleoside base, said process comprising hydrolyzing and reducing or reducing and hydrolyzing an iodopyrazolopyrimidine nucleoside of the formula:

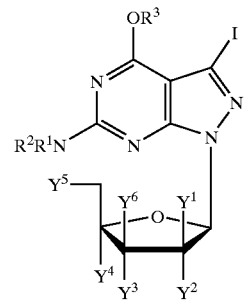

under conditions sufficient to produce a hydropyrazolopyrimidine nucleoside of the formula:

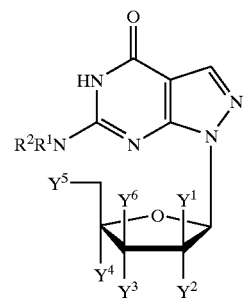

wherein
  $R^1$ is selected from the group consisting of hydrogen and alkyl;
  $R^2$ is selected from the group consisting of hydrogen, alkyl, and an amine protecting group, or $R^1$ and $R^2$ together form an amine protecting group;
  $R^3$ is selected from the group consisting of alkyl, and a hydroxy protecting group; and
  each of $Y^1$, $Y^2$, $Y^3$, $Y^4$, $Y^5$, and $Y^6$ is independently selected from the group consisting of hydrogen, halide, alkyl, —$OR^4$, wherein each $R^4$ is independently selected from the group consisting of hydrogen, alkyl, and a hydroxy protecting group or two $R^4$ groups form a diol protecting group, or $Y^2$ and $Y^4$ together with the carbon atoms to which they are attached to and C-3 carbon atom of the carbohydrate ring form a five-to seven membered ring.

14. The process of claim 13, wherein $R^1$, $R^2$, $Y^1$, $Y^2$, $Y^4$, and $Y^6$ are hydrogen, and $Y^3$ and $Y^5$ are —$OR^4$.

15. The process of claim 14, wherein $R^4$ are hydrogen.

16. The process of claim 15 further comprising producing a PPG phosphoramidite of the formula:

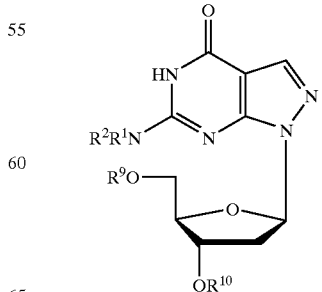

from said hydropyrazolopyrimidine nucleoside, wherein

R$^1$ is hydrogen and R$^2$ is an amine protecting group or R$^1$ and R$^2$ together form an amine protecting group; and one of R$^9$ and R$^{10}$ is a phosphoramidite and the other is a hydroxy protecting group, said PPG phosphoramidite producing step comprises:

(a) (i) contacting said hydropyrazolopyrimidine nucleoside with an amine protecting reagent under conditions sufficient to produce an amine-protected nucleoside of the formula:

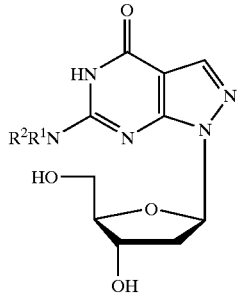

(ii) contacting said amine-protected nucleoside with a hydroxy protecting reagent under conditions sufficient to produce an amine/monohydroxy protected nucleoside of the formula:

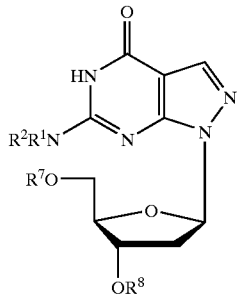

or i) contacting said hydropyrazolopyrimidine with a hydroxy protecting reagent under conditions sufficient to produce a monohydroxy protected nucleoside of the formula:

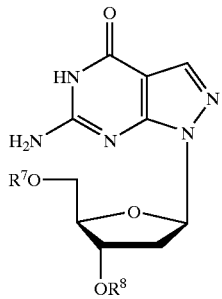

(ii) contacting said monohydroxy protected nucleoside with an amine protecting reagent under conditions sufficient to produce an amine/monohydroxy protected nucleoside of the formula:

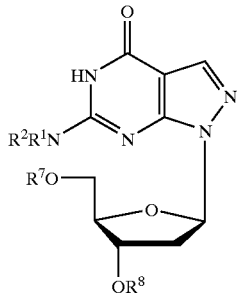

wherein

R$^1$ is hydrogen and R$^2$ is an amine protecting group or R$^1$ and R$^2$ together form an amine protecting group; and one of R$^7$ and R$^8$ is hydrogen and the other is a hydroxy protecting group; and (b) contacting said amine/monohydroxy protected nucleoside with an activated phosphoramidite under conditions sufficient to produce said PPG phosphoramidite.

17. The process of claim 16, wherein said amine protecting reagent is selected from the group consisting of N,N-dialkylformamide dialkylacetal, and N,N-dialkylacetamide dialkylacetal.

18. The process of claim 16, wherein said hydroxy protecting reagent is a photolabile hydroxy protecting reagent.

19. The process of claim 18, wherein said photolabile hydroxy protecting reagent is selected from the group consisting of 1-(3,4-methylenedioxy-6-nitrophenyl)ethyl chloroformate, 2-(2-nitrophenyl)-2-methylethyl chloroformate, 2-(2-nitro-6-chlorophenyl)-2-methylethylsulfonyl chloride and 3',5'-dimethoxybezoinoxyl chloroformate.

20. The process of claim 16, wherein said hydroxy protecting reagent is an acid labile hydroxy protecting reagent.

21. The process of claim 20, wherein said acid labile hydroxy protecting reagent is selected from the group consisting of trityl halide, monomethoxytrityl halide and dimethoxytrityl halide.

22. The process of claim 16, wherein said activated phosphoramidite is of the formula:

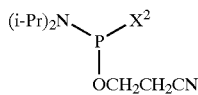

wherein

X$^2$ is a leaving group.

23. The process of claim 22, wherein X$^2$ is selected from the group consisting of halide and diisopropylamino.

24. The process of claim 22, wherein R$^9$ is dimethoxytrityl and R$^{10}$ is a phosphoramidite moiety of the formula —P[N(i-Pr)$_2$]OCH$_2$CH$_2$CN.

25. The process of claim 13 further comprising producing said nucleoside of Formula I, wherein said nucleoside of Formula I producing step comprises:

contacting an iodopyrazolopyrimidine of the formula:

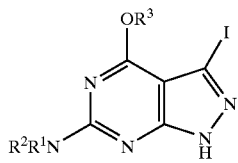

with an activated sugar of the formula:

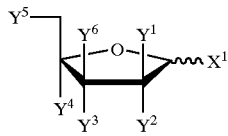

under conditions sufficient to produce said nucleoside of Formula I,
wherein
$R^1$, $R^2$, $R^3$, $Y^1$, $Y^2$, $Y^3$, $Y^4$, $Y^5$, and $Y^6$ are those defined claim 13; and
$X^1$ is a leaving group.

26. The process of claim 25 further comprising producing said iodopyrazolopyrimidine nucleoside of Formula I from a pyrimidinone of the formula:

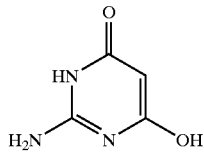

said iodopyrazolopyrimidine nucleoside producing process comprising:
(i) contacting said pyrimidinone with a halogenating agent and a formylating agent under conditions sufficient to produce a dihalopyrimidine carboxyaldehyde of the formula:

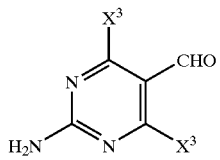

wherein
each $X^3$ is independently selected from the group consisting of F, Cl, Br and I;
(ii) contacting said dihalopyrimidine carboxyaldehyde with hydrazine under conditions sufficient to produce a halopyrazolopyrimidine of the formula:

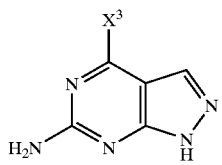

(iii) contacting said halopyrazolopyrimidine with an alkoxide of the formula $R^3$—OM, wherein $R^3$ is alkyl and M is a metal, to produce an alkoxypyrazolopyrimidine of the formula:

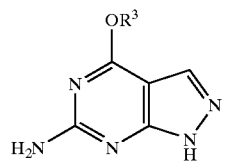

and
(iv) iodinating said alkoxypyrazolopyrimidine with an iodinating agent under conditions sufficient to produce said iodopyrazolopyrimidine.

27. The process of claim 26, wherein said halogenating agent is selected from the group consisting of $POCl_3$, iodine monochloride, N-iodosuccinamide and $SOCl_2$.

28. The process of claim 26, wherein said formylating agent is a compound comprising a formyl group attached to a secondary amino group.

29. The process of claim 28, wherein said formylating agent is selected from the group consisting of dimethyl formamide, 1-formylpiperidine, 1-formylmorpholine and triformamide.

30. The process of claim 26, wherein said iodinating agent is selected from the group consisting of iodine monochloride and N-iodosuccinimide.

31. A process for producing a nucleoside comprising:
(a) contacting an iodopyrazolopyrimidine of the formula:

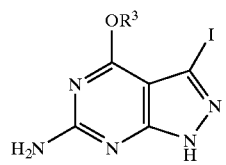

with an activated sugar of the formula:

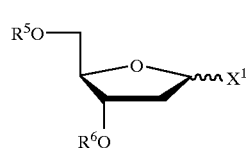

under conditions sufficient to produce an deoxy iodopyrazolopyrimidine nucleoside of the formula:

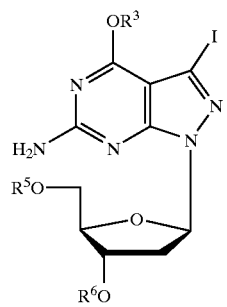

(b) producing an amino dihydro hydropyrazolopyrimidine nucleoside from said deoxy iodopyrazolopyrimidine nucleoside, wherein said amino dihydro hydropyrazolopyrimidine nucleoside is of the formula:

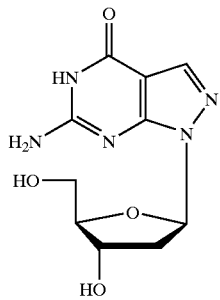

wherein $R^3$ is alkyl;

$R^5$ and $R^6$ are hydroxy protecting groups; and $X^1$ is a leaving group.

32. The process of claim 31, wherein said step of producing said amino dihydro hydropyrazolopyrimidine nucleoside comprises removing said hydroxy protecting groups $R^5$ and $R^6$; hydrolyzing —$OR^3$ group; and reducing the iodine.

33. The process of claim 31 further comprising:

(c) contacting said amino dihydro hydropyrazolopyrimidine nucleoside with an amine protecting reagent under conditions sufficient to produce an amine protected nucleoside of the formula:

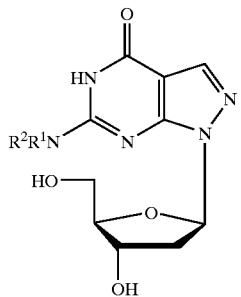

(d) contacting said amine protected nucleoside with a hydroxy protecting reagent under conditions sufficient to produce an amine/monohydroxy protected nucleoside of the formula:

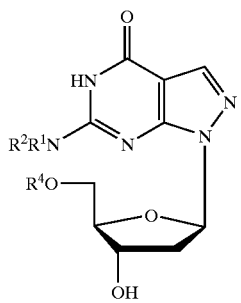

and (e) contacting said amine/monohydroxy protected nucleoside with an activated phosphoramidite of the formula:

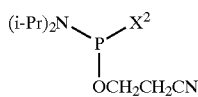

under conditions sufficient to produce a PPG phosphoramidite of the formula:

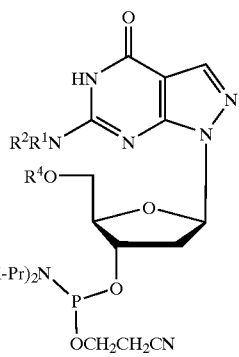

wherein $R^1$ is hydrogen;

$R^2$ is an amine protecting group;

or $R^1$ and $R^2$ together form an amine protecting group;

$R^4$ is a hydroxy protecting group; and $X^2$ is a leaving group.

34. The process of claim 33, wherein $X^2$ is selected from the group consisting of halide, and —$N(i\text{-}Pr)_2$.

35. The process of claim 33, wherein $R^1$ and $R^2$ together form a nitrogen protecting group of the formula: =CH—$N(CH_3)_2$.

36. The process of claim 35, wherein $R^4$ is selected from the group consisting of an acid labile hydroxy protecting group and a photolabile hydroxy protecting group.

37. The process of claim 36, wherein $R^4$ is selected from the group consisting of dimethoxytrityl, trityl, pixyl, 1,1-bis(4-methoxyphenyl)-1-pyrenylmethyl, α-methyl-6-nitropiperonyloxycarbonyl, 2-(2-nitrophenyl)-2-methylethoxycarbonyl, 2-(2-nitro-6-chlorophenyl)-2-methylethylsulfonyl and 3',5'-dimethoxybezoinoxycarbonyl.

38. The process of claim 31, wherein said step (b) comprises reducing the iodide by hydrogenation.

39. The process of claim 31, wherein said iodopyrazolopyrimidine is produced from a pyrimidinone of the formula:

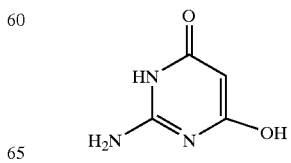

said iodopyrazolopyrimidine producing step comprising:

(i) contacting said pyrimidinone with a halogenating agent and a formylating agent under conditions sufficient to produce a dihalopyrimidine carboxyaldehyde of the formula:

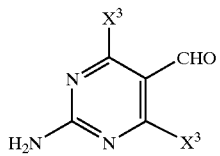

wherein each $X^3$ is independently selected from the group consisting of F, Cl, Br and I;

(ii) contacting said dihalopyrimidine carboxyaldehyde with hydrazine under conditions sufficient to produce a halopyrazolopyrimidine of the formula:

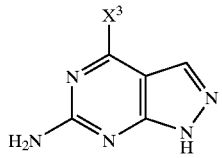

(iii) contacting said halopyrazolopyrimidine with an alcohol of the formula $R^3$—OH to produce an alkoxypyrazolopyrimidine of the formula:

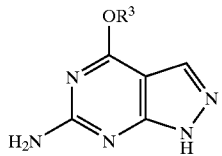

and (iv) iodinating said alkoxypyrazolopyrimidine with an iodinating agent under conditions sufficient to produce said iodopyrazolopyrimidine.

40. The process of claim 39, wherein said halogenating agent is selected from the group consisting of $POCl_3$, iodine monochloride, N-idosuccinamide and $SOCl_2$.

41. The process of claim 40, wherein said halogenating agent is selected from the group consisting of $POCl_3$ and $SOCl_2$.

42. The process of claim 39, wherein said formylating agent is selected from the group consisting of dimethyl formamide, 1-formylpiperidine, 1-formylmorpholine and triformamide.

43. The process of claim 39, wherein said iodinating agent is selected from the group consisting of iodine monochloride and N-iodosuccinimide.

44. The PPG phosphoramidite according to claim 1, wherein $R_2$ is a photolabile amine protecting group, or $R^1$ and $R^2$ together form a photolabile amine protecting group.

45. The PPG phosphoramidite according to claim 2, wherein $R_2$ is a photolabile amine protecting group, or $R^1$ and $R^2$ together form a photolabile amine protecting group.

46. The PPG phosphoramidite according to claim 3, wherein $R_2$ is a photolabile amine protecting group, or $R^1$ and $R^2$ together form a photolabile amine protecting group.

47. A PPG phosphoramidite comprising a hydroxy protecting group, wherein said phosphoramidite nucleoside is of the formula:

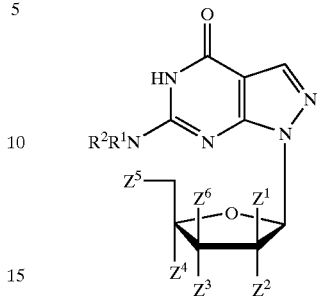

wherein $R^1$ is selected from the group consisting of hydrogen and alkyl;

$R^2$ is selected from the group consisting of hydrogen, alkyl, and an amine protecting group, or $R^1$ and $R^2$ together form an amine protecting group;

each of $Z^1$, $Z^2$, $Z^4$, and $Z^6$ is independently selected from the group consisting of hydrogen, halide, alkyl, —$OR^{11}$, wherein each $R^{11}$ is independently selected from the group consisting of hydrogen, alkyl, and a hydroxy protecting group or two $R^{11}$ groups form a diol protecting group, or $Z^2$ and $Z^4$ together with the carbon atoms to which they are attached and C-3 carbon atom of the carbohydrate ring form a five-to seven membered ring; and $Z^3$ is —$OR^{12}$ and $Z^5$ is —$OR^{13}$, where $R^{12}$ is a photolabile hydroxy protecting group and $R^{13}$ is a phosphoramidite.

48. The PPG phosphoramidite according to claim 47 of the formula:

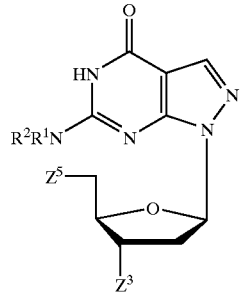

wherein $R^1$, $R^2$, $Z^3$ and $Z^5$ are those defined in claim 47.

49. The PPG phosphoramidite according to claim 47, wherein $R^2$ is a photolabile amine protecting group, or $R^1$ and $R^2$ together form a photolabile amine protecting group.

50. The PPG phosphoramidite according to claim 48, wherein $Z^3$ is $OR^{12}$ and $R^{12}$ is a photolabile hydroxy protecting group.

51. The PPG phosphoramidite according to claim 50, wherein $R^1$ and $R^2$, taken together with the nitrogen atom to which they are bonded, form a dimethylaminoformamidine group.

52. The PPG phosphoramidate having the formula:

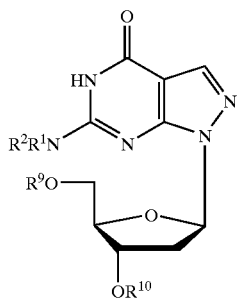

wherein $R^1$ is hydrogen and $R^2$ is an amine protecting group, or $R^1$ and $R^2$ together form an amine protecting group, $R^9$ is a phosphoramidite, and $R^{10}$ is a hydroxy protecting group.

53. The PPG phosphoramidite according to claim 52, wherein the amine protecting group is an acid-labile protecting group.

54. The PPG phosphoramidite according to claim 53, wherein $R^1$ and $R^2$ together form an acid-labile amine protecting group, and $R^{10}$ is an acid-labile hydroxy protecting group.

55. The PPG phosphoramidate according to claim 54, wherein $R^1$ and $R^2$, taken together with the nitrogen atom to which they are bonded, form a dimethylaminoformamidine group.

56. The PPG phosphoramidate according to claim 55, having the formula:

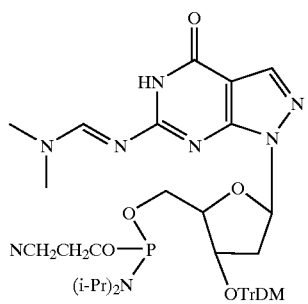

wherein "DMTr" represents a dimethoxytrityl group.

* * * * *